United States Patent [19]

Frisch et al.

[11] Patent Number: 4,853,026
[45] Date of Patent: Aug. 1, 1989

[54] HERBICIDAL EMULSIONS

[75] Inventors: Gerhard Frisch, Wehrheim; Konrad Albrecht, Kelkheim, both of Fed. Rep. of Germany

[73] Assignee: Hoechst Aktiengesellschaft, Frankfurt am Main, Fed. Rep. of Germany

[21] Appl. No.: 44,444

[22] Filed: Apr. 30, 1987

[30] Foreign Application Priority Data

May 2, 1986 [DE] Fed. Rep. of Germany ....... 3614788

[51] Int. Cl.[4] .............................................. A01N 25/22
[52] U.S. Cl. .......................................... 71/86; 71/116; 71/120; 71/DIG. 1; 71/9
[58] Field of Search ............................... 71/85, DIG. 1

[56] References Cited

U.S. PATENT DOCUMENTS 4,594,096  6/1986  Albrecht et al. ........................ 71/93

FOREIGN PATENT DOCUMENTS 0006293  1/1980  European Pat. Off. .
0070702  1/1983  European Pat. Off. .
0117999  9/1984  European Pat. Off. .
0118759  9/1984  European Pat. Off. .
0130370  1/1985  European Pat. Off. .

*Primary Examiner*—Catherine L. Mills
*Attorney, Agent, or Firm*—Curtis, Morris & Safford

[57] ABSTRACT

The present application describes herbicidal agents, based on emulsions, which contain two or more active compounds - a water-soluble, salt-like active compound and an active compound which is soluble in organic solvents - a surfactant mixture and a solvent, the surfactant mixture comprising a combination of phenylsulfonate salts, ethoxylated alkyl- (or polyaryl)phenol phosphates, ethoxylated acidic phohsphoric acid esters and alkylphenol polyglycol ether derivatives. These agents are prepared by the action of high shear forces.

4 Claims, No Drawings

HERBICIDAL EMULSIONS

The present invention relates to herbicidal agents in the form of prepared formulations based on emulsions. Prepared formulations are desirable, for example, when it is known, from appropriate preliminary biological experiments, that the action of the combination can be broadened compared to the individual active compounds.

EP-A 117,999 discloses formulations in the form of aqueous codispersions which contain an active compound concentrate based on alkyl phthalates as solvent in combination with an aqueous suspension concentrate.

Surprisingly, it has now been found that aqueous solutions of salt-like active compounds together with organic solutions of active compounds and selected surfactant mixtures produce stable emulsions.

The present invention therefore relates to herbicidal compositions based on organic solvents, water, surfactants and two or more active compounds, which compositions contain a water-soluble salt-like active compound, an active compound which is soluble in organic solvents, and a surfactant mixture, comprising a combination of (a) a phenylsulfonate salt,
(b) an ethoxylated alkylphenol phosphate or a polyarylphenol phosphate,
(c) an ethoxylated acidic phosphoric acid ester and
(d) an alkylphenol polyglycol ether derivative.

Suitable active compounds are the salts of glufosinate (U.S. Pat. No. 4,168,963), bialophos (U.S. Pat. No. 4,309,208), phosalacine (S. Omura et al., The Japanese Journal of Antibiotics, 37(2), p. 542 (1985)), paraquat (GB-A 813,531) and glyphosate (U.S. Pat. No. 3,799,758).

Suitable salts for the active compounds mentioned are, in particular, alkali metal salts, alkaline-earth metal salts, ammonium salts or ($C_1$-$C_7$)alkyl-substituted ammonium salts.

Suitable active compounds which are dissolved in organic solvents are, in particular, urea derivatives, such as linuron and monolinuron, or acetanilide compounds, such as metolachlor or alachlor, herbicidal phenoxy derivatives or active compounds having a similar range of action and which are soluble in the organic solvents mentioned below or are naturally liquid.

Preferred organic solvents are aromatic solvents, such as toluene, xylene, 1/2-methylnaphthalene, mixtures of $C_6$-$C_{16}$-aromatic compounds, such as, for example, the ®Solvesso series (Esso) with the types ®Solvesso 100 (boiling point 162°-177° C.), ®Solvesso 150 (boiling point 187°-207° C.) and ®Solvesso 200 (boiling point 219°-282° C.), ($C_1$-$C_{12}$)alkyl phthalates, specific ($C_4$-$C_8$)alkyl phthalates, water-immiscible ketones, such as, for example, cyclohexanone or isophorone, or ($C_6$-$C_{20}$)aliphatic compounds, which may be linear or cyclic, such as the products of the ®Shellsoll series, types T and K, or BP n-paraffins or liquid polyols, such as propylene glycol, ethylene glycol or glycerol.

Preferred surfactants to be employed according to the invention are:

(a) amongst the phenylsulfonates, in particular the alkali metal salts, for example ®Dispersant GN (Na phenylsulfonate, Rhône Poulenc), (b) amongst the ethoxylated alkyl- (or polyaryl)-phenol phosphates, for example ®Soprophor FL (ethoxylated polyarylphenol phosphate neutralized with triethanolamine, Rhône Poulenc), Hoe S 3475 (phosphated tristyrylphenol ethoxylate, Hoechst AG), Emphos CS 1512 (alkylated phenol ethoxylate, phosphated, Witco Chemical S.A.), ®Soprophor 3-D-33 (phosphated tristyrylphenol ethoxylate, Rhône Poulenc), (c) amongst the ethoxylated acidic phosphoric acid esters, for example ®Gafac RM 410 (GAF Corp.), (d) amongst the alkylphenol polyglycol ethers, for example ®Sapogenat T (Hoechst AG), ®Rewomul CSF 20 (cetostearyl alcohol with 20 EO (EO=ethylene oxide units), REWO, Chem. Group), ®Rewomul MG (glycerol monostearate, REWO, Chem. Group), ®Rewopal PO (ethylenepropylene oxide block polymer, REWO, Chem. Group), ®Emulpon EL 40 (Witco Chemical S.A.), ®Emulsogen EL series (ethoxylated castor oil, Hoechst AG), ®Comperlan LMD (laurylmyristyldiethanolamide, Henkel), ®Comperlan COD (coconut oil diethanolamide, Henkel) and ®Atlox 4885 (sorbitan trioleate, ICI, Atlas Chemie).

The surfactant composition for the herbicidal composition according to the invention generally comprises 0.1-4.5% by weight, preferably 0.5-2.0% by weight, of phenylsulfonate salts, 1-10% by weight, preferably 3.5-6% by weight, of ethoxylated alkyl- (or polyaryl)-phenol phosphates, 0.1-2% by weight, preferably 0.4-0.7% by weight, of ethoxylated acidic phosphoric acid esters, and 1-8% by weight, preferably 2-6% by weight, of alkylphenol polyglycol ethers.

Water, the salt-like, water-soluble active compound and a phenylsulfonate salt preferably form the aqueous phase, and an organic solvent, the active compound, ethoxylated alkyl- (or polyaryl)phenol phosphate, ethoxylated acidic phosphoric acid ester and alkylphenol polyglycol ether preferably form the organic phase.

The prepared formulation can contain 1-60% by weight of active compound, 3-30% by weight of surfactant and 0-75% by weight of solvent.

The ratio of active compounds in the aqueous phase to active compounds in the organic phase can be 10:1 to 1:10, but preferably 1:1 to 1:5 and very particularly 1:1 to 1:3.5.

Both phases—the aqueous and the organic—are stirred together and then subjected to shear forces in the range 10 to 7,000 sec$^{-1}$, as occur, for example, in colloid mills (PUC, Fryma), static mixers (®Erestat), turbo stirrers (Ultraturax, IKA; Polytron, Kinematica) or in similar equipment. During this procedure, the oil-in-water emulsion which is still present on mixing surprisingly becomes a water-in-oil emulsion which, in contrast to other water-in-oil emulsions, is absorbed very well by water to again form an oil-in-water emulsion in the water. These water-in-oil emulsions are particularly stable on storage, have very good applicational properties and permit water-soluble active compounds and such organic solvent-soluble active compounds to be combined to form excellent prepared formulations.

The aqueous phase to organic phase ratio varies between 20:80 and 60:40, but preferably between 35:65 and 50:50. The fact that water-in-oil emulsions are present here can be confirmed very well on the one hand by microscopic observations by means of stained phases, and on the other hand by conductivity measurements.

In order to improve the viscosity, aluminosilicates, such as ®Bentone SD-1, and similar substances can be added as thickeners to the mixture.

The surfactant mixtures are also suitable for preparing prepared formulations which contain only one of the active compounds mentioned.

In the table below, examples are shown which illustrate the process according to the invention.

TABLE

Formulation examples (component data in % by weight)

| Composition | 1 | 2 | 3 | 4 | 5 | 6 | 7 |
|---|---|---|---|---|---|---|---|
| Glufosinate | 9.33 | 9.33 | 9.33 | 9.33 | 9.33 | | |
| Glyphosate | | | | | | 3.3 | 3.3 |
| Metolachlor | | | | | | 7.7 | |
| Linuron | | | | | | | |
| Monolinuron | 14.0 | 14.0 | 14.0 | 14.0 | 14.0 | | 7.7 |
| Alachlor | | | | | | | |
| ® Dispersant GN | 1.0 | 1.0 | 1.2 | 0.5 | 1.0 | 0.5 | 0.5 |
| ® Soprophor FL/ ® Sapogenat | 5.0 | 4.0 | 4.0 | 5.0 | 4.5 | 5.0 | 5.0 |
| T 110 | 4.0 | 3.0 | 3.0 | 3.5 | 3.0 | 4.0 | 4.0 |
| ® Gafac RM 410 | 0.5 | 0.5 | 0.5 | 0.5 | 0.5 | 0.5 | 0.5 |
| ® Bentone SD-I | 0.1 | 0.1 | | 0.1 | | | |
| Dioctyl phthalate (DOP) | 36.0 | 40.0 | 40.0 | 38.0 | 38.0 | 72.0 | 72.0 |
| Isophorone | 14.0 | | | | | | |
| ® Solvesso 200 | | | 10.0 | | | | |
| ® Solvesso 100 | | | | 10.0 | | | |
| ® Solvesso 150 | | | | | 12.0 | | |
| Cyclohexanone | | 12.0 | | | | | |
| Water to 100% | | | | | | | |

® Dispersant GN: Na phenylsulfonate
® Soprophor FL: ethoxylated polyarylphenyl phosphate, neutralized with triethanolamine
® Sapogenat T110: triisobutylphenol polyglycol ether with about 11 EO
® Gafac RM410: ethoxylated acidic phosphoric acid esters
® Bentone SD-1: aluminum silicate
® Solvesso: mixtures of ($C_6$–$C_{16}$) aromatic compounds Solvesso 220 (boiling point 219–282° C.), Solvesso 100 (boiling point 162–177° C.), Solvesso 150 (boiling point 187–207° C.)

| Composition | 8 | 9 | 10 | 11 | 12 | 13 |
|---|---|---|---|---|---|---|
| Glufosinate | 14.3 | 12.8 | 12.5 | 5.0 | 16.4 | 15.0 |
| Glyphosate | | | | | | |
| Metolachlor | | | | 37.0 | 37.0 | |
| Linuron | | 12.8 | | | | |
| Monolinuron | 14.7 | | | | | 3.0 |
| Alachlor | | | 25.0 | | | |
| ® Dispersant GN | 1.0 | 1.0 | 1.0 | 2.5 | 1.0 | 0.5 |
| ® Soprophor FL | 6.0 | 6.0 | 5.0 | 5.0 | 5.0 | 5.0 |
| ® Sapogenat T110 | 4.0 | 4.0 | 4.0 | 4.0 | 4.0 | 4.0 |
| ® Gafac RM 410 | 0.5 | 0.5 | 0.5 | 0.5 | 0.5 | 0.5 |
| ® Bentone SD-I | 0.1 | 0.1 | | | | |
| Diocytl phthalate (DOP) | 40.0 | 5.0 | 21.0 | 10.8 | 10.8 | 42.0 |
| Isophorone | 10.0 | 30.7 | | | | |
| Water to 100% | | | | | | |

| Composition | 14 | 15 | 16 | 17 |
|---|---|---|---|---|
| Glufosinate | 13.3 | 13.3 | 15.6 | 15.6 |
| Glyphosate | | | | |
| Metolachlor | 32.0 | 32.0 | 35.0 | 35.0 |
| Linuron | | | | |
| Monolinuron | | | | |
| Alachlor | | | | |
| ® Dispersant GN | 2.0 | 2.0 | 1.0 | 1.0 |
| ® Soprophor FL | 5.0 | 5.0 | 3.5 | 6.5 |
| ® Sapogenat T110 | 3.0 | 3.0 | 5.5 | 2.5 |
| ® Gafac RM 410 | 0.5 | 0.5 | 0.5 | 0.5 |
| ® Bentone SD-I | | | 0.1 | 0.1 |
| Dioctyl phthalate (DOP) | | | 10.5 | 10.5 |
| Xylene | 21.0 | | | |
| ½ Methylnaphthalene | | 21.0 | | |
| Water to 100% | | | | |

| Composition | 18 | 19 | 20 | 21 | 22 | 23 | 24 |
|---|---|---|---|---|---|---|---|
| Glufosinate | 15.6 | 15.6 | 15.6 | 15.6 | 13.6 | 13.7 | 13.0 |
| Glyphosate | | | | | | | |
| Metolachlor | 35.0 | 35.0 | 35.0 | 35.0 | 30.8 | 30.8 | 30.0 |
| Linuron | | | | | | | |
| Monolinuron | | | | | | | |
| Alachlor | | | | | | | |
| ® Dispersant GN | 1.0 | 1.0 | 1.0 | 1.0 | 1.0 | 1.0 | 1.0 |
| ® Soprophor FL | 5.0 | 5.0 | 5.0 | 5.0 | 5.0 | 5.0 | 5.0 |
| ® Sapogenat T110 | | | | | 2.0 | 2.0 | 2.0 |
| ® Gafac RM 410 | 0.5 | 0.5 | 0.5 | 0.5 | 0.5 | 0.5 | 0.5 |
| ® Rewomul | 4.0 | | | | | | |
| CSF-20 | | | | | | | |
| ® Rewomul MG | | 4.0 | | | | | |
| ® Rewopal PO | 4.0 | | | | | | |
| ® Emulsogen EL 400 | | | 4.0 | | | | |
| ® Comperlan LMD | | | | 2.0 | | | |
| ® Comperlan COD | | | | | 2.0 | | |
| ® Atlox 4885 | | | | | | | 2.0 |
| ® Bentone SD-I | 0.1 | 0.1 | 0.1 | 0.1 | | | |
| Dioctyl phthalate(DOP) | 10.5 | 10.5 | 10.5 | 10.5 | 17.0 | 17.0 | 17.0 |
| Water to 100% | | | | | | | |

® Rewomul CSF-20: cetostearyl alcohol having 20 EO
® Rewomul MG: glycerol monostearate
® Rewopal PO: ethylenepropylene oxide block polymer
® Emulsogen EL 400: ethoxylated castor oil
® Comperlan LMD: laurylmyristyldiethanolamide
® Comperlan COD: coconut oil diethanolamide
® Atlox 4885: sorbitan trioleate

| Composition | 25 | 26 | 27 | 28 | 29 | 30 |
|---|---|---|---|---|---|---|
| Glufosinate | | 23.0 | 16.1 | 9.33 | 15.6 | 9.1 |
| Glyphosate | 5.0 | | | | | |
| Metolachlor | 12.0 | 9.6 | 36.2 | | 35.0 | |
| Linuron | | | | | | 9.1 |
| Monolinuron | | | | 14.0 | | |
| ® Dispersant GN | 0.5 | 1.0 | 1.0 | 1.0 | 1.0 | 1.0 |
| ® Soprophor Fl/ Hoe S 3475* | 5.0 | 5.0 | 5.0 | 4.0 | 5.0* | 5.0 |
| ® Sapogenat T110 | 4.0 | 4.0 | 4.0 | 5.0 | 4.0 | 5.0 |
| ® Gafac RM 410 | 0.5 | 0.5 | 0.5 | 0.5 | 0.5 | 0.5 |
| ® Bentone SD-I | | | 0.05 | | 0.1 | |
| Dioctyl phthalate (DOP) | 6.0 | 30.0 | 10.0 | 50.0 | 10.5 | 53.8 |
| Water to 100% | | | | | | |

| Composition | 31 | 32 | 33 | 34 |
|---|---|---|---|---|
| Glufosinate | 8.2 | 8.2 | 12.3 | 12.3 |
| Linuron | 8.2 | 8.2 | 8.2 | 8.2 |
| ® Dispersant GN | 1.0 | 1.0 | 1.0 | 1.0 |
| ® Soprophor FL | 5.0 | 5.0 | 5.0 | 5.0 |
| ® Sapogenat T110 | 5.0 | 5.0 | 5.0 | 5.0 |
| ® Gafac RM 410 | 0.5 | 0.5 | 0.5 | 0.5 |
| Dioctyl phthalate (DOP) | 58.2 | 48.2 | 50.4 | 46.4 |
| Water to 100% | | | | |

HOE S 3475: phosphated tristyrylphenol ethoxylate

We claim:

1. A herbicidal composition comprising an aqueous phase containing a water-soluble salt of a herbicide selected from the group consisting of glufosinate and glyphosate;
   an organic phase containing a herbicide being soluble in organic solvents, said herbicide selected from the group consisting of metolachlor, linuron, monolinuron and alachlor; and
   a surfactant mixture comprising 0.1 to 4.5% by weight of a phenylsulfonate salt, 1.0 to 10.0% by weight of an ethoxylated alkylphenol phosphate or polyarylphenol phosphate, 0.1 to 2.0% by weight of an ethoxylated acidic phosphoric acid ester and 1.0 to 8.0% by weight of an alkylphenol polyglycol ether,
   wherein the total amount of (a) the herbicides is 1 to 60% by weight, (b) the surfactant mixture is 3 to 30% by weight and (c) the solvent is 0 to 75% by weight, all the above weight ratios based on the total weight of the composition.

2. A herbicidal composition as claimed in claim 1, wherein the solvent is toluene, xylene, ½ methylnaphthalene, a mixture of $C_6$–$C_{16}$-aromatic compounds, a phthalate or a water-immiscible ketone.

3. A herbicidal composition as claimed in claim 1, wherein the aqueous to organic phase ratio is 20:80 to 60:40.

4. A herbicidal composition as claimed in claim 1, which additionally contains alumino-silicates as thickeners.

* * * * *